(12) United States Patent
Takatori et al.

(10) Patent No.: US 11,576,591 B2
(45) Date of Patent: Feb. 14, 2023

(54) GAS SENSOR KIT AND GAS SUPPLY UNIT

(71) Applicant: Nihon Kohden Corporation, Tokyo (JP)

(72) Inventors: Fumihiko Takatori, Tokyo (JP); Masayuki Inoue, Tokyo (JP); Kenichiro Kabumoto, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 1097 days.

(21) Appl. No.: 16/087,310

(22) PCT Filed: Jun. 2, 2017

(86) PCT No.: PCT/JP2017/020706
§ 371 (c)(1),
(2) Date: Sep. 21, 2018

(87) PCT Pub. No.: WO2017/217264
PCT Pub. Date: Dec. 21, 2017

(65) Prior Publication Data
US 2019/0099110 A1   Apr. 4, 2019

(30) Foreign Application Priority Data

Jun. 14, 2016 (JP) .............................. JP2016-117777

(51) Int. Cl.
*A61B 5/097*      (2006.01)
*A61B 5/00*       (2006.01)
*A61M 16/06*      (2006.01)

(52) U.S. Cl.
CPC ............ *A61B 5/097* (2013.01); *A61B 5/6803* (2013.01); *A61B 5/6819* (2013.01);
(Continued)

(58) Field of Classification Search
CPC .......... A61M 16/0666; A61M 16/0672; A61M 16/0677; A61M 16/0841; A61M 16/085;
(Continued)

(56) References Cited

U.S. PATENT DOCUMENTS 6,190,327 B1 * 2/2001 Isaacson .............. A61B 5/0836
                                                              250/353
6,629,934 B2 * 10/2003 Mault .................. A61B 5/4866
                                                              128/204.26
(Continued)

FOREIGN PATENT DOCUMENTS

CN      104189985 A    12/2014
CN      104398242 A     3/2015
(Continued)

OTHER PUBLICATIONS

International Search Report issued in Patent Application No. PCT/JP2017/020706 dated Sep. 22, 2017.
(Continued)

*Primary Examiner* — Valerie L Woodward
(74) *Attorney, Agent, or Firm* — Pearne & Gordon, LLP (57) ABSTRACT

A gas sensor kit includes a gas sensor that measures a gas concentration of an exhalation gas of a subject and a gas supply unit that supplies a therapeutic gas, supplied through a tube, to the subject. In the gas sensor, the gas sensor has a convex portion that is supported when connected with the gas supply unit, and the gas supply unit has at least one locking claw that supports the convex portion when connected with the gas sensor.

10 Claims, 13 Drawing Sheets

(52) U.S. Cl.
CPC . *A61M 16/0672* (2014.02); *A61B 2560/0443* (2013.01); *A61M 2202/0208* (2013.01); *A61M 2230/43* (2013.01)

(58) Field of Classification Search
CPC ........ A61M 2016/103; A61M 2230/43; A61M 2230/432; A61M 2202/0208; A61B 5/097; A61B 5/6819; A61B 5/6803; A61B 2560/0443
See application file for complete search history.

(56) References Cited

U.S. PATENT DOCUMENTS

| | | | |
|---|---|---|---|
| 7,445,602 | B2 | 11/2008 | Yamamori et al. |
| 2002/0029003 | A1 | 3/2002 | Mace et al. |
| 2002/0122746 | A1 | 9/2002 | Yamamori et al. |
| 2009/0088657 | A1 | 4/2009 | Yamamori et al. |
| 2010/0317987 | A1 | 12/2010 | Inoue et al. |
| 2011/0094513 | A1 | 4/2011 | Takatori et al. |
| 2014/0066800 | A1* | 3/2014 | Takatori ............... A61B 5/0836 600/543 |
| 2015/0099986 | A1* | 4/2015 | Inoue .................... A61B 5/082 600/479 |
| 2015/0342502 | A1* | 12/2015 | Saeki ............... A61M 16/0841 600/537 |
| 2017/0028154 | A1 | 2/2017 | Takatori et al. |
| 2017/0196512 | A1 | 7/2017 | Inoue |

FOREIGN PATENT DOCUMENTS

| | | |
|---|---|---|
| CN | 104548304 A | 4/2015 |
| EP | 2 859 845 A1 | 4/2015 |
| EP | 2 952 862 A1 | 9/2015 |
| JP | 2003-315264 A | 11/2003 |
| JP | 5385599 B2 | 1/2014 |
| JP | 2015-073751 A | 4/2015 |
| JP | 2015-226698 A | 12/2015 |
| WO | 2014-193847 A1 | 12/2014 |

OTHER PUBLICATIONS

Written Opinion issued in Patent Application No. PCT/JP2017/020706 dated Sep. 22, 2017.
Nihon Kohden Corporation, "CO2 Sensor Kit", URL: http://www.nihonkohden.co.jp/iryo/products/monitor/01_bedside/tg970p.html. Accessed May 31, 2016.
Japanese Office Action issued in Japanese Patent Application No. 2016-117777 dated May 27, 2020.
Chinese Office Action issued in Chinese Patent Application No. 201780020035.3 dated Sep. 1, 2020.
European Office Action dated Feb. 17, 2022 issued in European Patent Application No. 17 731 953.0.

* cited by examiner

GAS SENSOR KIT AND GAS SUPPLY UNIT

TECHNICAL FIELD

The present invention relates to a gas sensor kit and a gas supply unit, and particularly to a gas sensor kit which performs an exhalation gas concentration measurement and a therapeutic gas administration, and a gas supply unit.

BACKGROUND ART

As a symptomatic therapy with respect to a subject in a low-oxygen state, a method administering high concentration oxygen gas with an oxygen mask or an oxygen cannula is used. In the case of performing a treatment with respect to the subject in the low-oxygen state, it is necessary to perform both the administration of the high concentration oxygen gas and the measurement of a respiratory state (exhalation gas concentration) of the subject.

PTL 1 discloses a bite block which accurately measures the respiratory state of the subject by avoiding an effect of secretion such as saliva. The bite block includes a cylindrical first wall having a hole into which a conduit is inserted, a second wall which encloses the first wall and opposes an oral cavity, and a gas flow path to a sample port which is configured by a gap between the first wall and the second wall (FIGS. 1 and 2 in PTL 1). The bite block is configured such that the respiration information collection adapter is attachable therein and detachable therefrom, and a prong is attached in the respiration information collection adapter (FIG. 4 in PTL 1). Further, oxygen is supplied to the prong from an oxygen supplying source (paragraph [0024] in PTL 1).

CITATION LIST

Patent Literature

[PTL 1]
Japanese Patent No. 5385599

Non Patent Literature

[NPL 1]
"CO2 sensor kit", Accessed: May 31, 2016], Internet URL: "http://www.nihonkohden.co.jp/iryo/products/monitor/01_bedside/tg970p.html"

SUMMARY OF INVENTION

Technical Problem

In a medical field, an oxygen administration into a nostril may be performed or be suspended in the middle of a therapy according to a purpose of the therapy or a change of a condition. However, in the configuration of PTL 1, since the oxygen administration is performed through a prong which is a fine pipe, it is difficult to perform attachment and detachment in the middle of the therapy. In addition, there is a risk that the prong is erroneously closed at the time of attaching and detaching. For this reason, a gas supply unit is needed which can be simply attached to and detached from a respiration information collection adapter including a gas sensor.

The above case is not limited to the oxygen administration, and commonly occurs in a case where another therapeutic gas such as a hydrogen gas is used.

In this regard, the present invention has been made in consideration of the above case, and a main object thereof is to provide a gas supply unit which can be simply attached to and detached from a gas sensor and a gas sensor kit provided with the gas supply unit.

Solution to Problem

According to an aspect of the invention, a gas sensor kit includes a gas sensor that measures a gas concentration of an exhalation gas of a subject and a gas supply unit that supplies a therapeutic gas, supplied through a tube, to the subject. In the gas sensor, the gas sensor has a convex portion that is supported when connected with the gas supply unit, and the gas supply unit has at least one locking claw that supports the convex portion when connected with the gas sensor.

With the above-described configuration of the gas sensor kit, the gas supply unit is connected with the gas sensor with through the locking claw. By the operation of fitting the locking claw and the convex portion, it is possible to easily attach and detach the gas supply unit to/from the gas sensor.

Advantageous Effects of Invention

The present invention can provide a gas sensor kit including a gas supply unit which can be simply attached to and detached from a gas sensor.

DESCRIPTION OF EMBODIMENTS

First Embodiment

Hereinafter, the embodiment of the present invention will be described with reference to drawings. In the drawings, the same components are denoted by the same reference numerals and the same names, and the redundant explanation is not repeated. In addition, the size or the shape of each of components is described with a suitable adjustment in order to facilitate understanding of the present invention.

Figure 1:
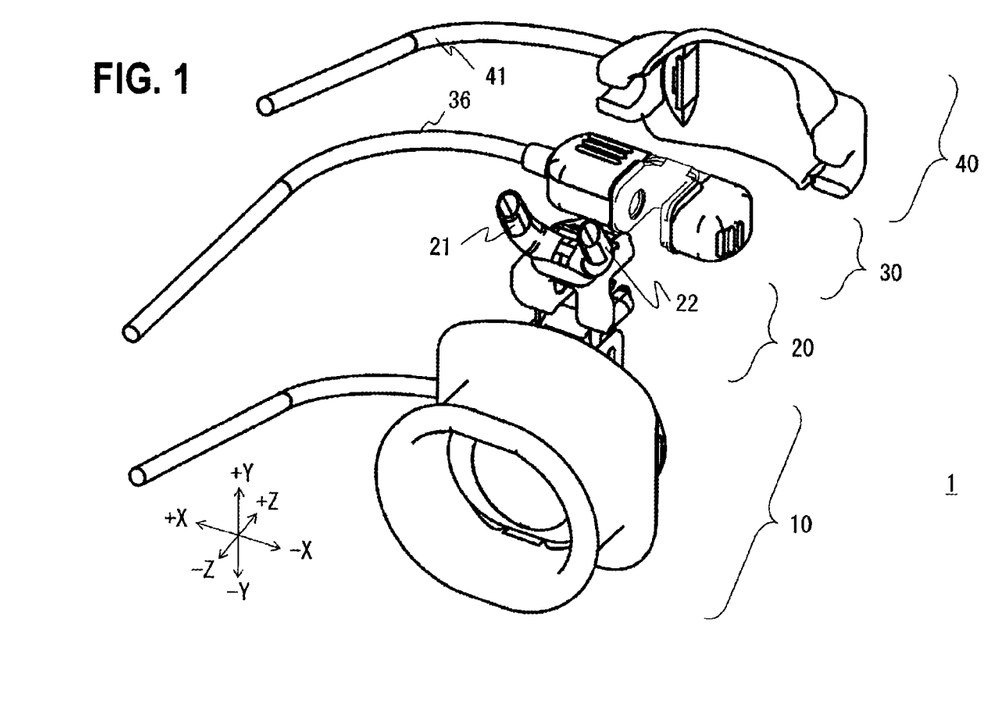
FIG. 1 is an exploded perspective view schematically illustrating a gas sensor kit 1 according to a first embodiment.

FIG. 1 is an exploded perspective view schematically illustrating a gas sensor kit 1 according to this embodiment. The gas sensor kit 1 insufflates a therapeutic gas to a subject, and is a medical unit which measures an exhalation gas concentration. The gas sensor kit 1 includes a bite block 10, a nasal adapter 20, a gas sensor 30, and a gas supply unit 40. The therapeutic gas may be an oxygen gas or a hydrogen gas, and in the following description, an oxygen gas is adopted.

Incidentally, in the following description and drawings, the directions when the gas sensor kit 1 is attached on the subject are determined as follows. A right and left direction of a face of the subject when a state where the gas sensor kit 1 is attached on the subject is viewed from a front side is set as an X direction (a left-face direction is a positive X direction, and a right-face direction is a negative X direction). An upper and lower direction of the face of the subject is set as a Y direction (a vertex direction is a positive Y direction, and a chin direction is a negative Y direction). An intraoral direction of the subject is set as a negative Z direction, and a direction away from an oral cavity of the subject is set as a positive Z direction.

The bite block 10 is a tool which is inserted into the oral cavity when an inspection is performed by using an endoscope or a hard mirror. Incidentally, the bite block 10 is an example of the tool which is disposed in the vicinity of the oral cavity of the subject and is used together with the gas supply unit 40. For this reason, the gas sensor kit 1 may include a mask or the like instead of the bite block 10. The bite block 10 has a cylindrical shape, and has a connection mechanism which is connected with the nasal adapter 20.

The nasal adapter 20 is connected with the bite block 10, and is an adapter which is disposed in the vicinity of nostrils of the subject. Nasal tubes 21 and 22 are inserted into both nostrils of the subject. In addition, the nasal adapter 20 is connected with the gas sensor 30, and the exhalation gas of the subject is introduced to the gas sensor 30. That is, the nasal adapter 20 is one aspect of a gas introduction part which introduces the exhalation gas of the subject to the gas sensor 30.

The gas sensor 30 is configured to be attachable to and detachable from the nasal adapter 20. For example, the gas sensor 30 is connected with the nasal adapter 20 by fitting a concave portion 35 which will be described later having a light receiving window to the nasal adapter 20. The gas sensor 30 measures the concentration of the carbon dioxide in the exhalation gas. The concentration of the carbon dioxide is one example and the gas sensor 30 may other gas concentration. The gas sensor 30 has a light-emitting part and a light-receiving part, and calculates the concentration of the carbon dioxide based on the transmitted light of the exhalation gas of the subject. Since the carbon dioxide has a property to absorb strongly an infrared ray of a certain specific wavelength, the infrared light is strongly absorbed as the concentration of the carbon dioxide in the exhalation gas is higher, and the amount of the transmitted light is decreased. The gas sensor 30 may have any shape or structure as long as the concentration of the carbon dioxide of the exhalation gas is detected by using the property. The gas sensor kit disclosed in NPL 1 is an example as implementation.

The gas sensor 30 is configured to be attachable to and detachable from the gas supply unit 40. A connection structure of the gas sensor 30 and the gas supply unit will be described later with reference to FIG. 9.

Figure 6:
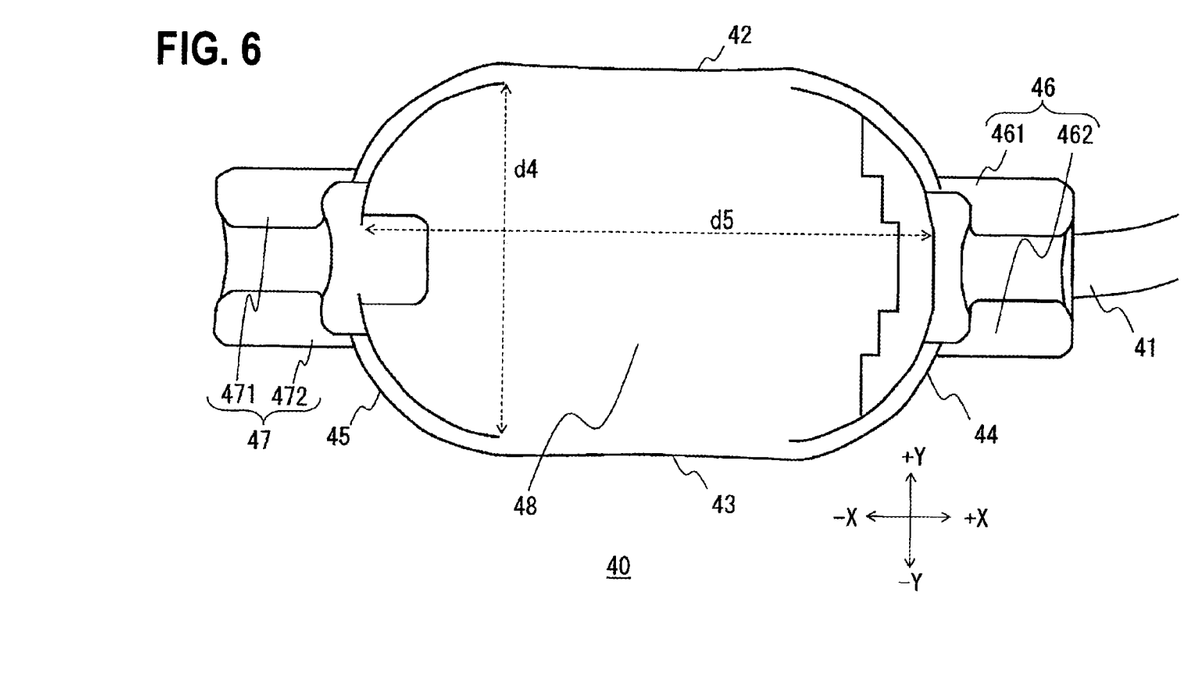
FIG. 6 is an appearance view of the gas supply unit 40 according to the first embodiment.

The gas supply unit 40 is connected with the nasal adapter 20 through the gas sensor 30, and is disposed in the vicinity of the nostril of the subject. The oxygen gas is supplied from an oxygen supplying source to the tube 41. The gas supply unit 40 has a cap-shaped (cup-shaped) main body 43 to cover the casing of the gas sensor 30. The cap-shape (cup-shape) of the main body 43 is shown in FIG. 6 and will be described later.

Figure 2:
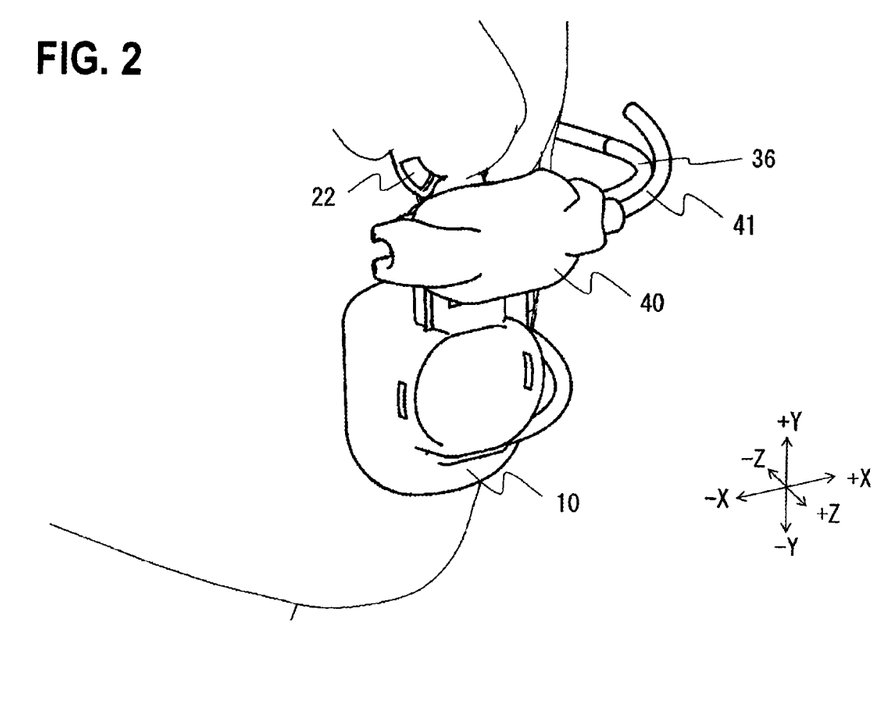
FIG. 2 is a conceptual view illustrating a state where the gas sensor kit 1 according to the first embodiment is mounted.

Subsequently, the description will be given about the state where the gas sensor kit 1 is attached. FIG. 2 is a view illustrating the state where the gas sensor kit 1 according to this embodiment is attached. That is, an enlarged view of a lower portion of the face of the subject on is shown in which the gas sensor kit 1 is being attached.

The bite block 10 is inserted into the oral cavity of the subject. The nasal tubes 21 (not illustrated in FIG. 2) and 22 of the nasal adapter 20 connected to the bite block 10 are inserted into both nostrils of the subject. The nasal tubes 21 and 22 may be disposed in a vicinity of the nostrils.

The gas supply unit 40 covers the main body of the nasal adapter 20 and the gas sensor 30, and is disposed between the nostril and a lip of the subject. The gas supply unit 40 supplies the oxygen gas supplied from the tube 41 to the vicinity of the nostril of the subject.

Figure 3:
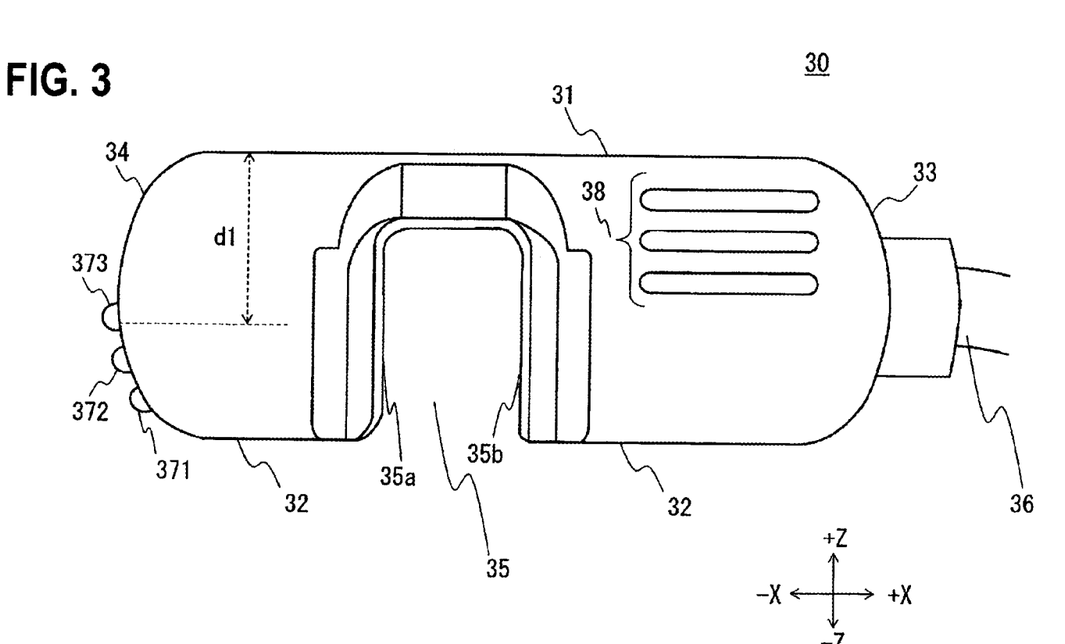
FIG. 3 is an appearance view of a gas sensor 30 according to the first embodiment.

Subsequently, the description will be given about a structure of a gas sensor 30. FIG. 3 is a top view of the gas sensor 30 (a view when the gas sensor 30 is seen from a positive Y direction). The gas sensor 30 has an elongated shape which includes major axes 31 and 32 and minor axes 33 and 34. As illustrated in the drawing, the minor axis 33 and the minor axis 34 may have a curved shape, but a linear shape is not excluded.

A concave recess 35 to be fitted with a nasal adapter 20 is provided in the major axis 32. A light-emitting element which can emit infrared light is provided in one of a side surface 35a and a side surface 35b of the recess 35, and a light-receiving element which can receive the infrared light is provided in the other one. The nasal adapter 20 introduces an exhalation gas of a subject to the recess 35. The light-receiving element outputs a signal according to a strength of the detected infrared light. An absorption rate of the infrared light is varied according to an exhalation gas concentration, and thus a signal indicating an infrared intensity reflects the exhalation gas concentration. The output signal is sent to an external device through a cable 36. The gas sensor 30 may have a mechanism which processes the output signal to detect the exhalation gas concentration therein.

The minor axis 33 is connected with the cable 36 connected with the external device. The cable 36 extends from the minor axis 33 of the gas sensor 30, and is connected with an external device such as a biological information monitor through a connector and the like. The minor axis 34 is positioned in a surface opposed to the minor axis 33 attached with the cable 36. Convex portions 371 to 373 for locking which are locked at the time of connection with the gas supply unit 40 are provided in the minor axis 34. In the following description, the common description in the convex portions 371 to 373 is simply described as a convex portion 37. That is, the convex portion 37 is provided in a surface (minor axis 33) opposed to an attachment surface (minor axis 34) of the cable 36 extending from the gas sensor 30. Incidentally, the number of the convex portion 37 is arbitrary. In addition, a plurality of projections 38 in which a finger is caught when the gas sensor 30 is gripped may be provided in a casing surface of the gas sensor 30. A depth d1 from the convex portion 37 to the major axis 31 will be described later with reference to FIG. 9. In this embodiment, the minor axis is at one end of the gas sensor and the minor axis 34 is at the other end of the gas sensor. The other end is opposite side with respect to the one end.

The casing of the gas sensor 30 is made, for example, of plastic. The casing of the gas supply unit 40 has a rigidity enough not to be deformed, and has a structure which is slightly bent when the gas sensor 30 is pressed.

Figure 4:
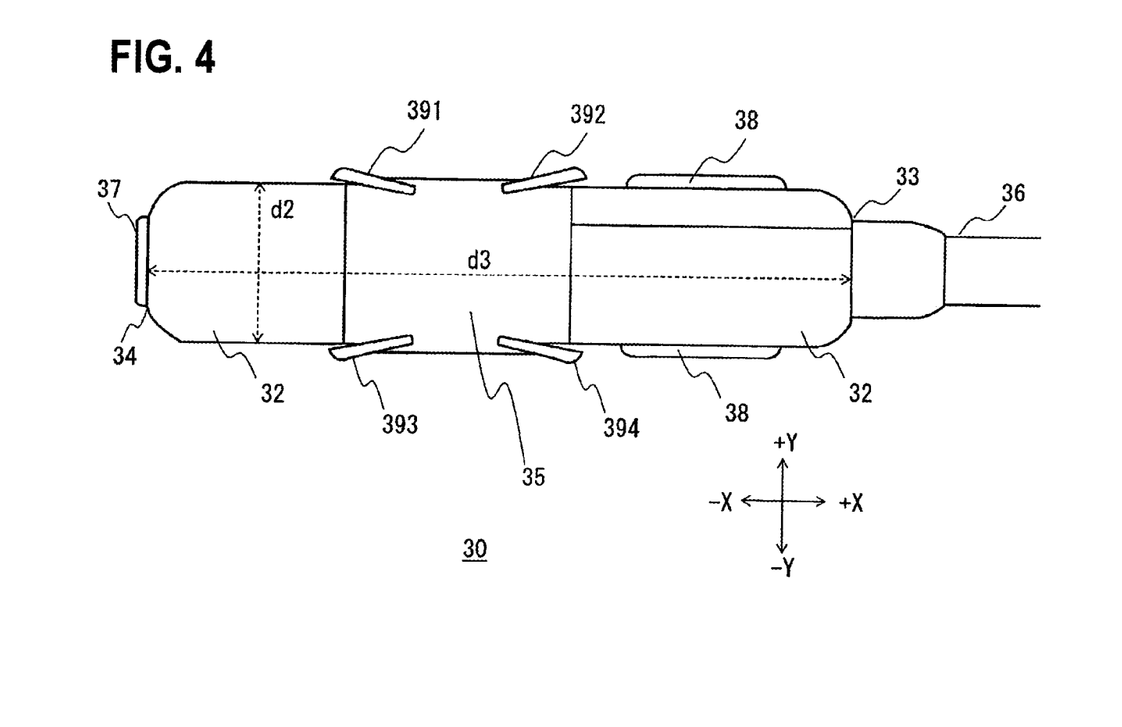
FIG. 4 is an appearance view of the gas sensor 30 according to the first embodiment.

FIG. 4 is a back view of the gas sensor 30 (a view when the gas sensor 30 is seen from a negative Z direction). As described above, the minor axis 33 is connected with the cable 36. The convex portion 37 for locking which is locked at the time of connection with the gas supply unit 40 is provided in the minor axis 34. As illustrated in the drawing, the convex portion 37 is convex in a direction (negative X direction) away from a main body of the gas sensor 30. Incidentally, a position regulating part 39 (391 to 394), which embraces a boss of the nasal adapter 20 and the like and fixes the position of the gas sensor 30 when fitted in the nasal adapter 20, may be provided in the recess 35.

A size (d2 and d3 in FIG. 4) of the gas sensor 30 is such a magnitude that is housed in a gap 48 of the gas supply unit 40 (to be described later). Accordingly, the gas supply unit 40 can be connected to the gas sensor and cover the gas sensor 30 (see FIG. 1).

Figure 5:
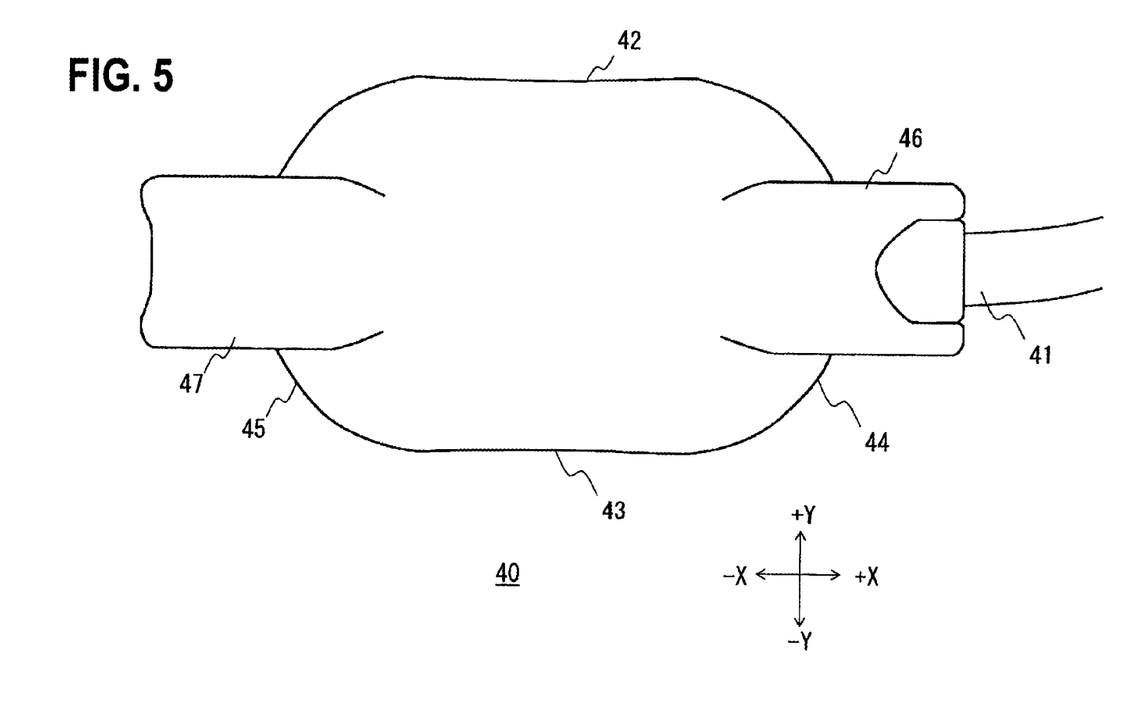
FIG. 5 is an appearance view of a gas supply unit 40 according to the first embodiment.

Next, the description will be given about the structure of the gas supply unit 40. FIG. 5 is a front view of the gas supply unit 40 (a view when the gas supply unit 40 is seen from the positive Z direction). The shape of the gas supply unit 40 has substantially linear major axes 42 and 43 and curved minor axes 44 and 45, and has an elongated shape. Connection parts 46 and 47 are provided in the minor axes 44 and 45, respectively. The shape of the connection parts 46 and 47 will be described later with reference to FIG. 7 or 8. Incidentally, the minor axes 44 and 45 may not necessarily have a curved shape, and may be a shape substantially corresponding to the elongated shape of the gas sensor 30.

FIG. 6 is a back view of the gas supply unit 40 (a view when the gas supply unit 40 is seen from the negative Z direction). The gas supply unit 40 has an elongated shape having the major axes (42 and 43) and the curved minor axes (44 and 45) as described above. As illustrated in FIG. 1, the gas supply unit 40 has a cap shape to cover the gas sensor 30, and the oxygen gas flows in the gap 48. The connection part 46 has a pair of locking claws 461 and 462. The locking claws 461 and 462 are provided in the same surface (minor axis 44) as an attachment surface of the tube 41 extending from the gas supply unit 40. Similarly, a connection part 47 has a pair of locking claws 471 and 472. The locking claws 471 and 472 are provided in the surface (minor axis 45) opposed to the attachment surface of the tube 41 extending from the gas supply unit 40. The gap 48 has a cap shape (a shape which covers the gas sensor 30 as illustrated in FIG. 1). The casing of the gas supply unit 40 is configured of a material having a rigidity such as plastic.

The gap 48 is a space into which the gas sensor 30 is inserted. For this reason, the size (d4 and d5 in FIG. 6) of the gap 48 is set to a magnitude corresponding to the gas sensor 30. For example, the magnitude is that the gas sensor 30 is fitted smoothly when inserted therein, and that can cover and hold the gas sensor 30.

Figure 7:
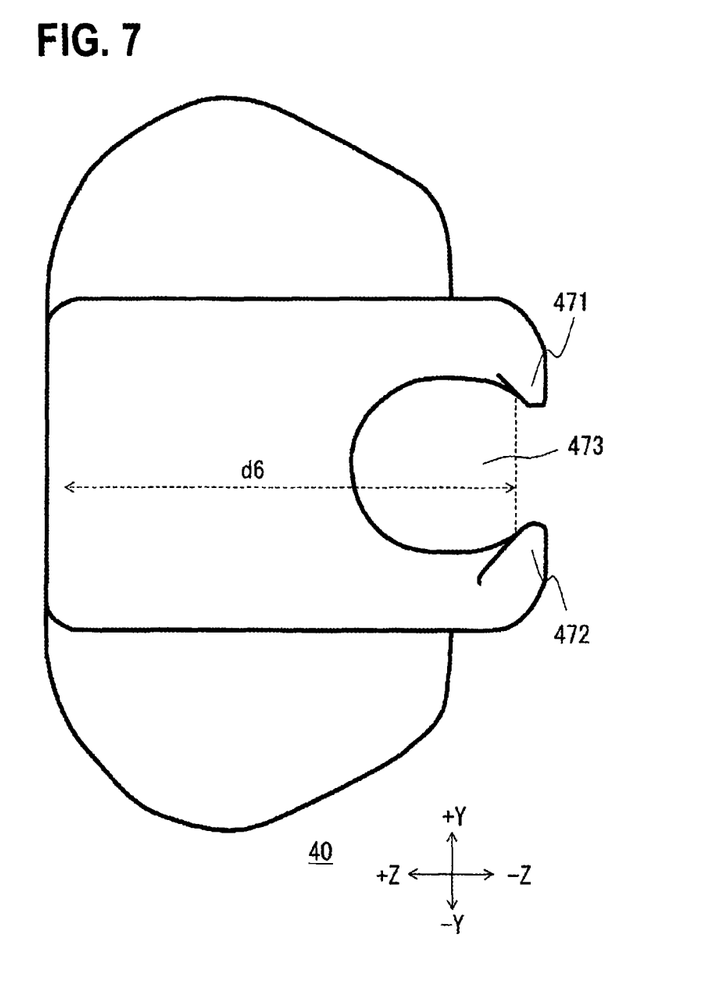
FIG. 7 is an appearance view of the gas supply unit 40 according to the first embodiment.

FIG. 7 is a left side view of the gas supply unit 40 (a view when the gas supply unit 40 is seen from the negative X direction). The connection part 47 has the pair of locking claws 471 and 472 which are convex to be supported from the upper and lower direction (upper: positive Y direction, lower: negative Y direction) in a negative Z side end. In addition, a locking hole 473 is provided which is concave and has the locking claws 471 and 472 as ends. The convex portion 37 of the gas sensor 30 is inserted into the locking hole 473. The insertion of the convex portion 37 will be described later with reference to FIG. 9, and the description will be given about a depth d6 from a bottom surface to the locking claws 471 and 472.

Figure 8:
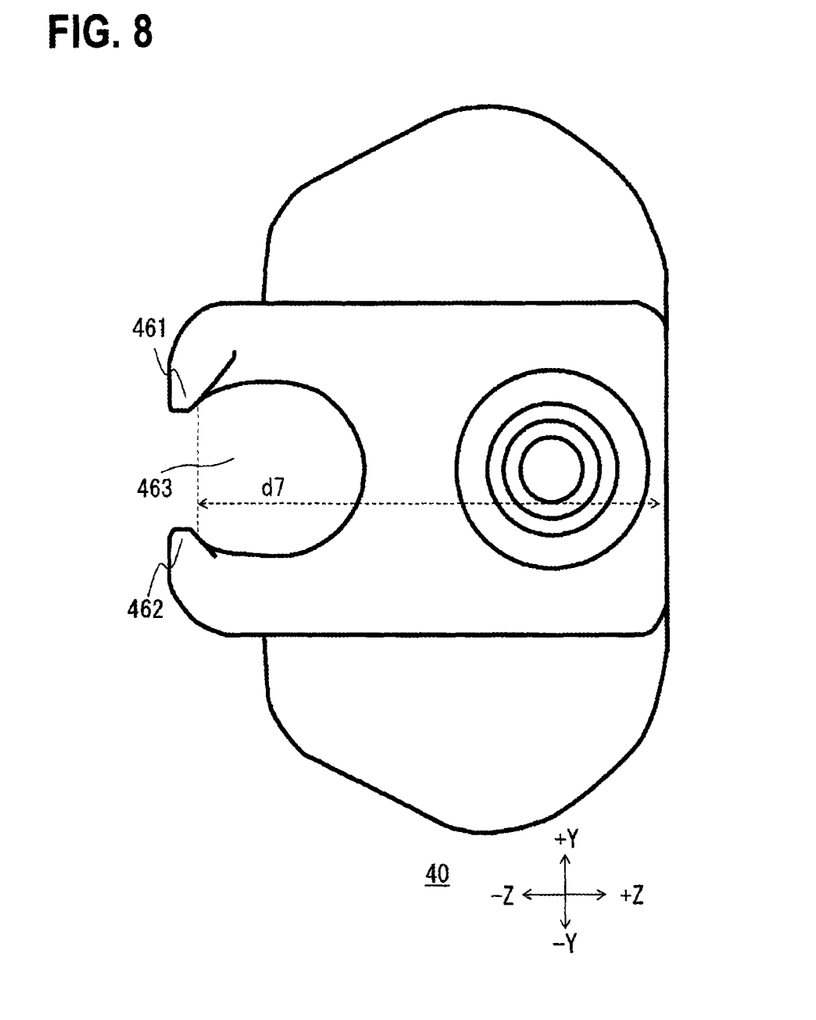
FIG. 8 is an appearance view of the gas supply unit 40 according to the first embodiment.

FIG. 8 is a right side view of the gas supply unit 40 (a view when the gas supply unit 40 is seen from the positive X direction). The connection part 46 has the pair of locking claws 461 and 462 which are concave from the upper and lower direction (upper: positive Y direction, lower: negative Y direction) in the negative Z side end so that the locking claws 461 and 462 can hold a predetermined member. In addition, a locking hole 463 is provided which is concave and has the locking claws 461 and 462 as ends. The convex portion 37 of the gas sensor 30 is inserted into the locking hole 463. The description of the insertion will be given later with reference to FIG. 9, and the description about a depth d7 from the bottom surface to the locking claws 461 and 462 will be given later.

Figure 9:
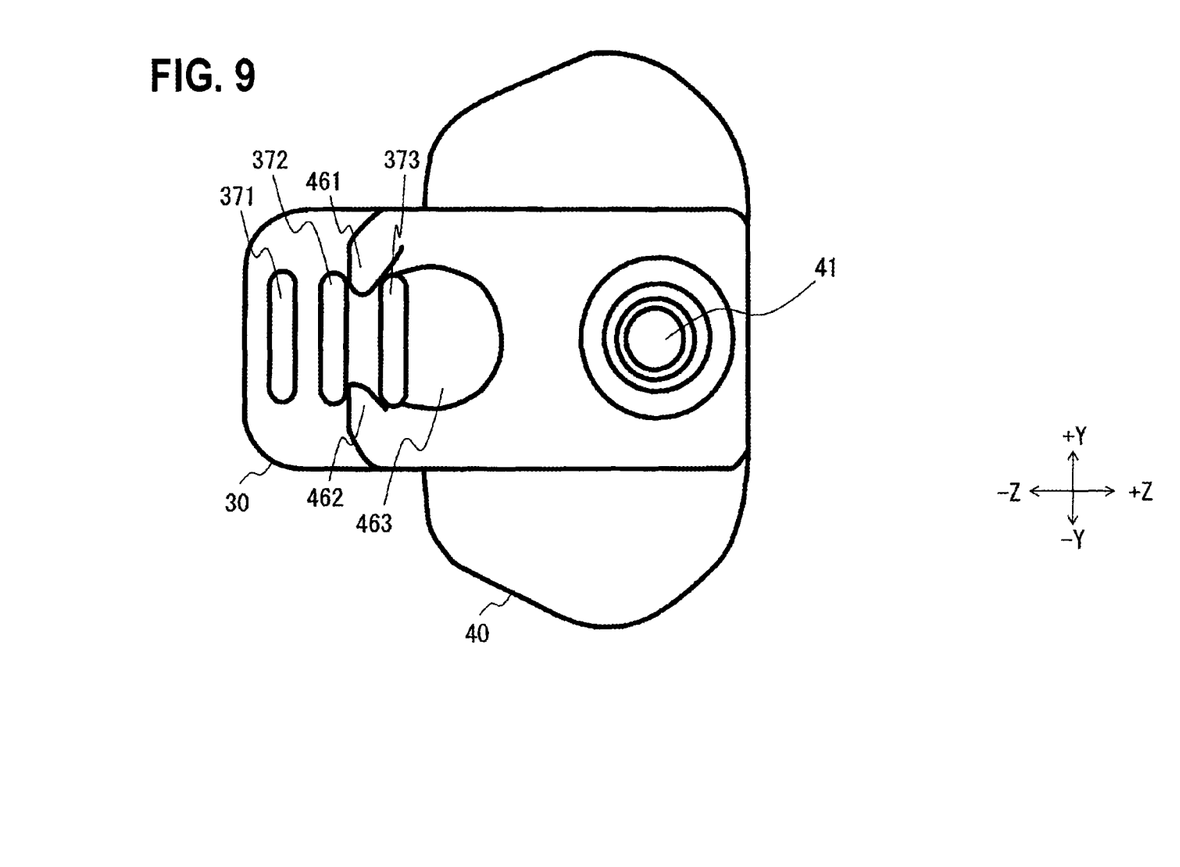
FIG. 9 is a view illustrating a connection form of the gas supply unit 40 and the gas sensor kit 30 according to the first embodiment.
Figure 10:
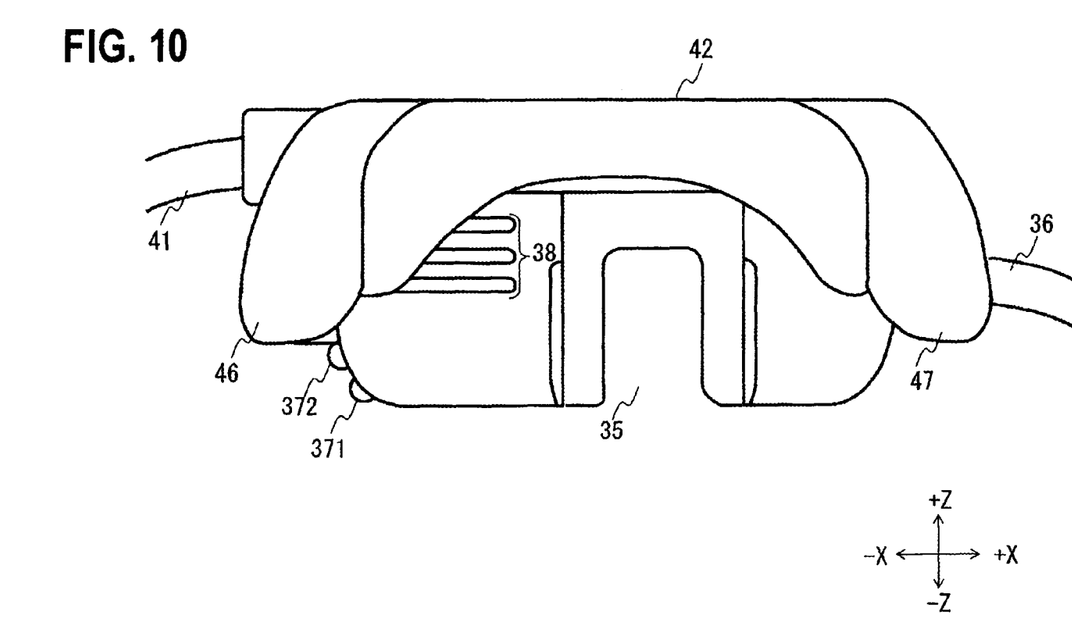
FIG. 10 is a view illustrating a connection form of the gas supply unit 40 and the gas sensor kit 30 according to the first embodiment.

Next, the description will be given about the connection structure of the gas sensor 30 and the gas supply unit 40. FIG. 9 is a right side view when the gas sensor 30 is connected with the gas supply unit 40 (a view when the gas sensor 30 and the gas supply unit 40 are seen from the positive X direction). In addition, FIG. 10 is a top view when the gas sensor 30 is connected with the gas supply unit 40 (a view when the gas sensor 30 and the gas supply unit 40 are seen from the positive Y direction). In an example of FIGS. 9 and 10, a configuration is disclosed in which a convex portion 373 of the gas sensor 30 is connected with the connection part 46. The convex portion 373 is hidden by the connection part 46 in FIG. 10.

The depth d1 which is a depth from the bottom surface (major axis 31) of the gas sensor 30 to the convex portion 373 in FIG. 3 is substantially the same as the depth d7 which is a height from the bottom surface (the end of the gap 48) of the gas supply unit 40 to the locking claws 471 and 472 in FIG. 8. For this reason, as illustrated in FIG. 9, the convex portion 373 of the gas sensor 30 is supported and held by the locking claws 461 and 462. In other words, the locking claws 461 and 462 supports the major axis of the convex portion 373 having an elongated and extended shape (FIGS. 4 and 9) from both ends so as to lock the convex portion 373. The gas supply unit 40 can tightly hold the gas sensor 30 from both sides through the locking by supporting the gas sensor 30 from both ends.

With reference to FIG. 10, the locking claws 461 and 462 (not illustrated in FIG. 10) are disposed in the same surface (minor axis 44) as the attachment surface of the tube 41. The locking claws 461 and 462 (not illustrated in FIG. 10) lock the convex portion 373 (not illustrated in FIG. 10). Accordingly, the tube 41 and the cable 36 are disposed to extend substantially in an opposite direction.

Figure 11:
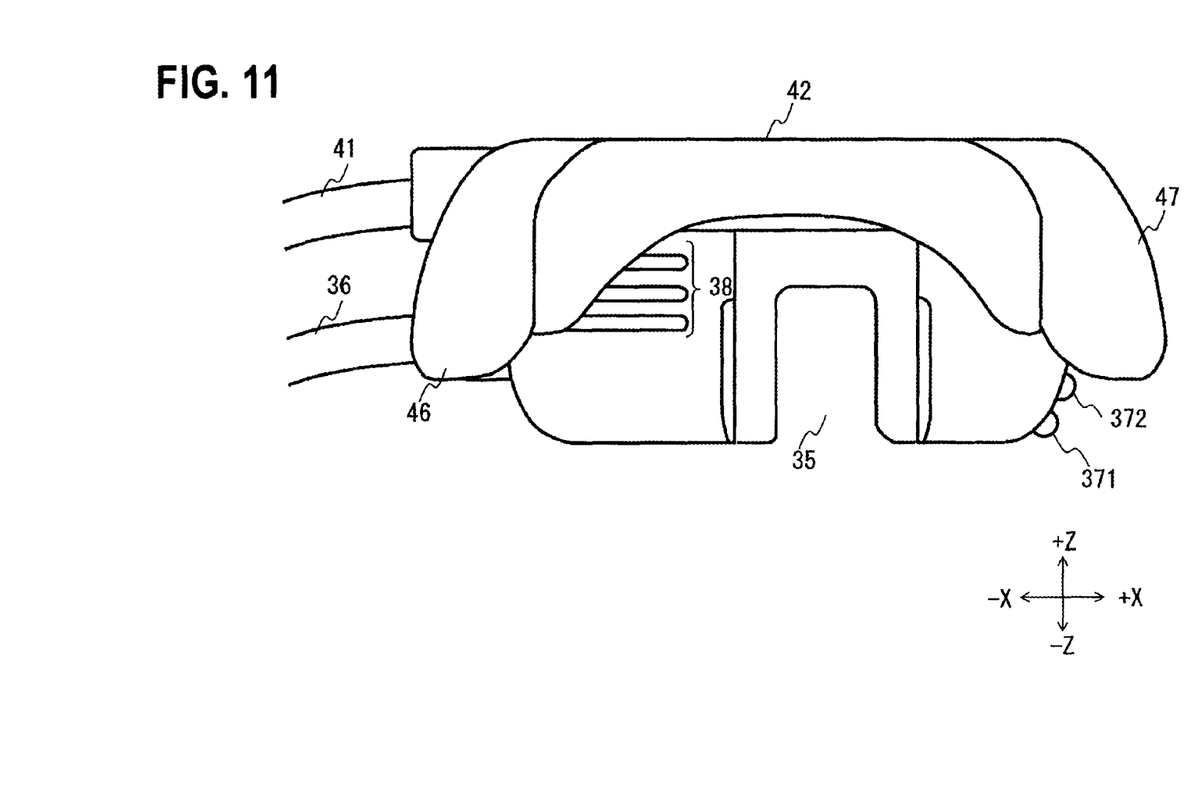
FIG. 11 is a view illustrating a connection form of the gas supply unit 40 and the gas sensor kit 30 according to the first embodiment.

FIG. 11 is a top view when the convex portion 373 of the gas sensor 30 is connected with the connection part 47. The top view is a view when seeing from the positive Y direction. The convex portion 373 is not shown in FIG. 10 as being hidden by the connection part 46. The locking claws 471 and 472 are provided in a surface (minor axis 45) opposed to the attachment surface (minor axis 44) of the tube 41. The locking claws 471 and 472 lock the convex portion 373 (not illustrated in FIG. 10). Accordingly, the tube 41 and the cable 36 are disposed to extend substantially in the same direction.

The depth d1 which is the depth from the bottom surface (major axis 31) of the gas sensor 30 to the convex portion 373 in FIG. 3 is substantially the same as the depth d6 which is the height from the bottom surface (the end of the gap 48) of the gas supply unit 40 to the locking claws 461 and 462 in FIG. 7. For this reason, as illustrated in FIG. 11, the tube 41 and the cable 36 can be connected to extend substantially in the same direction.

Subsequently, the description will be given about the effect of the gas sensor kit 1 according to this embodiment. The gas supply unit 40 is connected with the gas sensor 30 through the locking claws (461 and 462 or 471 and 472). By the operation of fitting the locking claw (461 and 462 or 471 and 472) and the convex portion 37, the gas supply unit 40 and the gas sensor 30 can be attached and detached easily. For this reason, although the oxygen administration is performed in the middle of any therapy, the oxygen administration can be performed with respect to the nostril without detaching the gas sensor 30.

The locking claws (461 and 462) are provided in the same surface (minor axis 44) as the attachment surface of the tube 41. When the convex portion 37 of the gas sensor 30 is connected by using the locking claws (461 and 462), the tube 41 and the cable 36 extend in different directions as illustrated in FIG. 10. Accordingly, the tube 41 and the cable 36 can be fixed by being hooked in both ears of the subject respectively. In addition, it is possible to easily cope with a case where an oxygen supplying source connected with the tube 41 and an external device connected with the gas sensor 30 are disposed on the both sides of a bed.

The locking claws (471 and 472) are provided in a surface (minor axis 45) opposed to the attachment surface of the tube 41. When the convex portion 37 of the gas sensor 30 is connected by using the locking claws (471 and 472), the tube 41 and the cable 36 extend substantially in the same direction as illustrated in FIG. 11. For example, in a case where the endoscope inspection is performed, it is assumed that the gas sensor kit 1 is used in a lateral recumbent position. Also in a case where the gas sensor kit 1 is used in the lateral recumbent position, since the tube 41 and the cable 36 extend in the same direction, the tube 41 and the cable 36 rarely disturb the inspection.

As illustrated in FIG. 6, the locking claws 461, 462, 471, and 472 of the gas supply unit 40 are provided in both the same surface (minor axis 44) as the attachment surface of the tube 41 and the opposing surface (minor axis 45). Accordingly, it is possible to easily change an extending direction of the tube 41 in the middle of the therapy. That is, it is possible to easily switch between the connection form of FIG. 10 and the connection form of FIG. 11.

As illustrated in FIG. 1, the gas supply unit 40 has a cap shape that covers the gas sensor 30. Accordingly, also in a case where the gas supply unit 40 is connected with the gas sensor 30, the gas sensor kit 1 can be compactly formed in a small concavo-convex shape. In addition, the gas supply unit 40 can be easily attached to the gas sensor 30 due to a cap shape that covers the gas sensor 30.

Hereinbefore, the invention made by this inventor is described in specific on the basis of the embodiment. However, the present invention is not limited to the above-described embodiment, and the invention may be modified variously without departing from the spirit and scope of the invention.

For example, a structure having only one of the connection part 46 and the connection part 47 may be adopted. Also in the structure, it is possible to easily attach and detach the gas supply unit 40 to/from the gas sensor 30.

In the above description, the locking claws of the gas supply unit 40 are described as a paired structure, but are not necessarily limited thereto. The locking claw provided in the gas supply unit 40 does not necessarily have a paired shape as long as the locking claw is engaged and connected with the convex portion 37 of the gas sensor 30, and may have such a shape that is engaged and fixed with the convex portion 37 from one direction.

Figure 12:
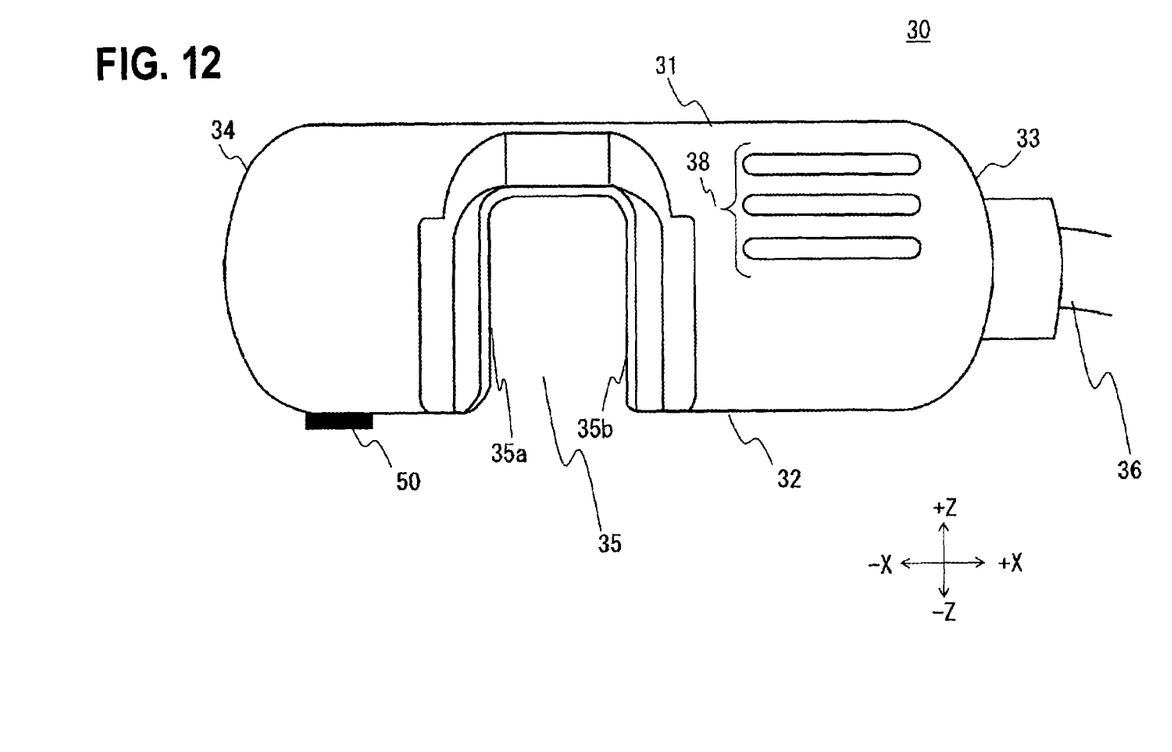
FIG. 12 is an appearance view of the gas sensor 30 according to the first embodiment.
Figure 13:
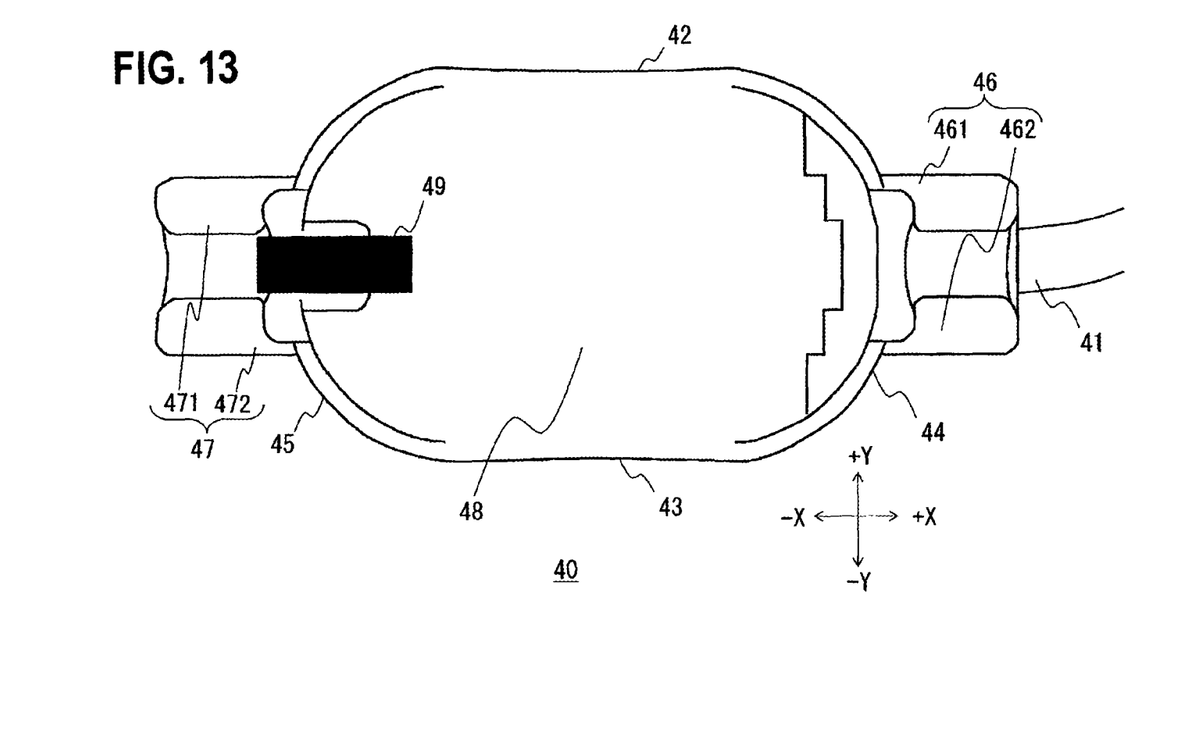
FIG. 13 is an appearance view of the gas supply unit 40 according to the first embodiment.

Each of the gas supply unit 40 and the gas sensor 30 may be configured to have an attachment and detachment mechanism which can fix each other and attach and detach each other. For example, a configuration may be adopted in which a protrusion is provided in the gas supply unit 40, and the protrusion can be fitted in the concave portion of the gas sensor 30. Alternately, a configuration may be adopted in which a concave portion is provided in the gas supply unit 40, and a protrusion is provided in the gas sensor 30. In addition, a configuration may be adopted in which a magnet is buried in each of the gas supply unit 40 and the gas sensor 30, and the gas supply unit 40 and the gas sensor 30 attract each other at the time of approaching so as to be connected. FIGS. 12 and FIG. 13 illustrate a configuration in which the gas supply unit and the gas sensor are fixed to each other by the magnet. The gas sensor 30 has a magnet 50 in the major axis 32 (FIG. 12). In addition, in the gas supply unit 40, a magnet 49 is provided in the gap 48 of the back surface. The gas sensor 30 and the gas supply unit 40 can be connected when the magnet 49 and the magnet 50 attract each other.

The present application is based on Japanese Patent Application No. 2016-117777, filed on Jun. 14, 2016, the entire contents of which are incorporated herein by reference.

INDUSTRIAL APPLICABILITY

There is provide a gas sensor kit including a gas supply unit which can be simply attached to and detached from a gas sensor.

REFERENCE SIGNS LIST 1 gas sensor unit
10: bite block
20: nasal adapter
21, 22: nasal tube
30: gas sensor
31, 32: major axis
33, 34: minor axis
35: recess
36: cable
37: convex portion
38: projection
391 to 394: position regulating part
40: gas supply unit
41: tube
42, 43: major axis
44, 45: minor axis
46, 47: connection part
461, 462, 471, 472: locking claw
48: gap
49: magnet
50: magnet

The invention claimed is:

1. A gas sensor kit comprising:
   a gas sensor that measures a gas concentration of an exhalation gas of a subject;
   a gas supply unit that supplies a therapeutic gas, supplied through a tube, to the subject, wherein
   the gas sensor has a convex portion that is supported when connected with the gas supply unit, and a cable attachment surface to which a cable is attached, and
   the gas supply unit has a pair of laterally disposed locking holes and a plurality of locking claws, wherein each locking claw partially defines an end of one of the locking holes, and wherein at least one locking claw supports the convex portion and at least one locking claw supports the cable when connected with the gas sensor.

2. The gas sensor kit according to claim 1, wherein the convex portion is provided on a surface opposed to the cable attachment surface.

3. The gas sensor kit according to claim 1, wherein:
   the gas supply unit includes a tube attachment surface to which a tube is attached, and
   at least one of the plurality of locking claws is provided on a surface opposed to the tube attachment surface.

4. The gas sensor kit according to claim 1, wherein:
   the gas supply unit includes a tube attachment surface to which a tube is attached, and
   at least one of the plurality of locking claws is provided in the same side as the tube attachment surface.

5. The gas sensor kit according to claim 1, wherein:
   the gas supply unit includes a tube attachment surface to which a tube is attached,
   at least four of the plurality of locking claws form two pairs of locking claws,
   a first pair of the locking claws is provided on the same side as the tube attachment surface, and
   a second pair of the locking claws is provided on a surface opposed to the tube attachment surface.

6. The gas sensor kit according to claim 1, wherein:
   the convex portion has an elongated and extended shape, and
   at least two of the plurality of locking claws form a paired structure with which a major axis of the extended shape is supported from both ends of the gas sensor.

7. The gas sensor kit according to claim 1, wherein a casing of the gas supply unit has a cap shape that covers a casing of the gas sensor.

8. A gas supply unit which is connected with a gas sensor which measures a gas concentration of an exhalation gas of a subject and supplies a therapeutic gas, supplied through a tube, to the subject, the gas supply unit comprising:
   a pair of laterally disposed locking holes,
   a plurality of locking claws, wherein each locking claw partially defines an end of one of the locking holes, and wherein at least one locking claw supports a convex portion provided in the gas sensor, and
   wherein the plurality of locking claws are provided on the same side of the gas supply unit as the side to which the tube is attached, and on a side opposite to the side to which the tube is attached.

9. A gas sensor kit comprising:
   a gas sensor that measures a gas concentration of an exhalation gas of a subject; and
   a gas supply unit that supplies a therapeutic gas, supplied through a tube, to the subject, wherein
   each of the gas supply unit and the gas sensor has an attachment and detachment mechanism by which the gas supply unit is capable of being attached to and detached from the gas sensor so that a direction of extension of the tube is reversible.

10. The gas sensor kit according to claim 9, wherein the attachment and detachment mechanism includes a magnet.

* * * * *